United States Patent [19]

Noppe et al.

[11] Patent Number: 5,441,896

[45] Date of Patent: Aug. 15, 1995

[54] SOLID PHASE ASSAY FOR USE WITH A PHYSICAL DEVELOPER

[76] Inventors: Marcus J. M. Noppe, Pater Antonissenstraat 14, B-2180-Kalmthout, Belgium; Theo C. Garrevoet, Kampioenstraat 14, B-2020-Antwerpen, Belgium

[21] Appl. No.: 73,961

[22] Filed: Jun. 8, 1993

Related U.S. Application Data

[63] Continuation of Ser. No. 809,030, Dec. 16, 1991, abandoned, which is a continuation of Ser. No. 532,702, Jun. 4, 1990, abandoned.

[30] Foreign Application Priority Data

Jun. 5, 1989 [EP] European Pat. Off. ........... 89201429

[51] Int. Cl.$^6$ ................ G01N 33/553; G01N 33/537; G01N 21/77
[52] U.S. Cl. .................... 436/525; 436/177; 436/178; 436/170; 436/541; 436/826; 435/962
[58] Field of Search ............... 436/525, 862, 177, 170; 435/962

[56] References Cited

U.S. PATENT DOCUMENTS

| | | | |
|---|---|---|---|
| 4,493,815 | 1/1985 | Fernwood et al. | 422/102 |
| 4,704,255 | 11/1987 | Jolley | 422/101 |
| 4,775,636 | 10/1988 | Moeremans | 436/518 |

OTHER PUBLICATIONS

Scopsi, L., "Silver–Enhanced Colloidal Gold Method", Hayat, Mass. *Colloidal Gold*, vol. 1, (Academic Press, NY) Chapter 9, 251-295 (1989).
Traina et al., Focus 5:5-6, 9 (1983).
Brada et al., Anal Biochem 142:79-83 (1984).
Danscher, G. "Autometallography", Histochemistry 81, 331-335 (1984).
Lackie, et al., "Investigation by Immunogold-Silver Staining by Electron Microscopy", Histochemistry 83, 545-550 (1985).

*Primary Examiner*—Michael P. Woodward

[57] ABSTRACT

The present invention is directed to a new assay procedure and improved solid phase assay devices for use with a so-called physical developer. The invention provides a new assay procedure for detecting the presence of an analyte in a fluid sample using a tracer having a metal label which signal is enhanced by applying a physical developer. The assay is performed with a device having a support for a test area and having attached thereto a binder specific for the analyte to be detected. The assay comprises the steps of directing the fluid sample and the tracer through a porous medium into contact with the test area at a controlled flow rate to allow binding of the analyte with the binder and the tracer to the analyte, directing a physical developer through said porous medium to amplify the signal generated by the tracer, and separating the device to allow the test area to be read. The invention further relates to devices and immunoassay test kits for carrying out the improved immunoassay procedure. A first device FIG. 2 according to the present invention has a support 4 having upper and lower surfaces and a test area on its upper surface. A removable filter 3 overlies the upper surface of the support. A second device FIG. 1 according to the present invention has a support 4 having upper and lower surfaces and a test area on its lower surface which is in contact with the absorptive layer 2.

7 Claims, 1 Drawing Sheet

SOLID PHASE ASSAY FOR USE WITH A PHYSICAL DEVELOPER

This is a continuation, of application Ser. No. 809,030, filed Dec. 16, 1991 which is a continuation of 07/532,702, filed Jun. 4, 1990 (abondoned).

BACKGROUND OF THE INVENTION

This invention relates to an assay for an analyte, and more particularly to a solid phase assay. In a solid phase assay, a binder specific for at least the ligand to be determined (analyte) is supported on a solid support, whereby, in the assay it is not necessary to employ an additional agent for separating the bound and free phases formed in the assay.

There are known in the art assays for analytes wherein the tracer employed in the assays includes a particular metal label, such as, a colloidal metal particle. Thus, for example, in such an assay, a binder specific for the analyte is supported on a solid support, and the tracer is comprised of a ligand specific for the analyte, which ligand of the tracer is labeled with a particular colloidal metal label. In such an assay, the tracer is indirectly attached to the binder on the solid support by binding of the analyte to the binder and binding of the tracer to the analyte, whereby the presence and/or amount of the analyte in a sample can be determined by detecting the presence and/or amount of colloidal metal tracer, which is indirectly bound to the binder on the solid support. A number of such assays are described in the European Patent Publication Nos. 158,746 and 293,947.

The signal generated by such a tracer can significantly be improved by subjecting the metal label indirectly bound to the surface of the solid phase to a so-called physical developing procedure.

The art-known physical developers generally consist of a solution containing a soluble metal salt, such as silver nitrate, a reducing agent, such as hydroquinone and an appropriate buffer system to establish a specific pH.

The European Patent Publication No. 158,746, page 10 lines 18 to 32, describes a method to improve the signal of a colloidal metal label significantly by subjecting the metal label indirectly bound to the surface of a blotting medium to a so-called physical developing procedure.

In case a silver based physical developer is applied the reduction of silver ions to metallic silver is catalyzed at the surface of the metal label, resulting in a specific deposition of metallic silver at the metal label site. In turn, the thus formed metallic silver particles catalyze the reduction, creating an auto-catalytic process. The effect of a physical development is that the reddish optical gold signal turns into a deep-brown to black silver signal, with a much higher intensity. The use of this art-known physical developer technique thus results in an improved signal, although there are a number of drawbacks associated with it.

One of the major problems in the use of physical developers is the solubility of the metal salts. Indeed, it is well known that metal ions, such as silver ions, form insoluble salts with many counter ions. Apart from depleting the available silver ion supply, these insoluble salts also form nuclei at which the reduction process is catalyzed as well, which results in a seriously augmented noise level. Moreover, silver ions may form light sensitive silver salts, such as silver bromide and silver chloride, which are readily reduced to metallic silver under the influence of light, starting an autocatalytic process. It is therefore absolutely necessary to work with extremely clean contacting surfaces, e.g. vessels, analytical grade chemicals and ultra-pure water. Usually it is also necessary to introduce multiple washing steps between the incubation with the metal tracer and the physical development of the label in order to remove unwanted ions present in the incubation medium. All this tends to make traditional physically developed metal-based assays more complex, expensive and error prone.

The major disadvantage of the traditional methods lies within the nature of physical developing itself. In the case of a silver-based physical developer, for example, the reducing agent reduces all silver ions at a certain rate. To obtain optimal sensitivity the amplification process has to be aborted by removing the physical developer from the metal label-containing phase before the non-label-induced reduction, the 'so-called selfnucleation', becomes apparent. It is obvious that physical developers become more flexible and powerful if the ratio between metal-specific reduction and self-nucleation can be increased. With the traditionally used assays, this ratio can hardly be augmented. The only parameter which can be modulated is the overall speed of the process; selfnucleation can be postponed only at the expense of a slower metal label amplification. One of the most obvious ways to do this is to change the concentration, nature or environment of the reducing agent. A frequently used approach is the use of hydroquinone at a pH lower than 4. The reducing action of hydroquinone is strongly inhibited in an acid environment; the user of the physical developer therefore has enough time to stop the metal label amplification before self-nucleation causes too much noise. However, acid additions are in many cases not compatible with the nature of the binding between the marked specific binding agent and its corresponding bindable substance. Most monoclonal antibodies have only a low or average affinity to their antigens at said pH. Moreover, no real gain in sensitivity can be accomplished because the label amplification is slowed down to the same degree as the self-nucleation is slowed down.

Thus there is a strong need for improving the sensitivity and practicality of metal based detection solid phase assays. Surprisingly it has been found that a severalfold increase in the ratio between the tracer bound signal and the self-nucleation can be obtained using the device described hereinafter, thus resulting in a higher sensitivity and speed.

DESCRIPTION OF THE INVENTION

Figure 1:
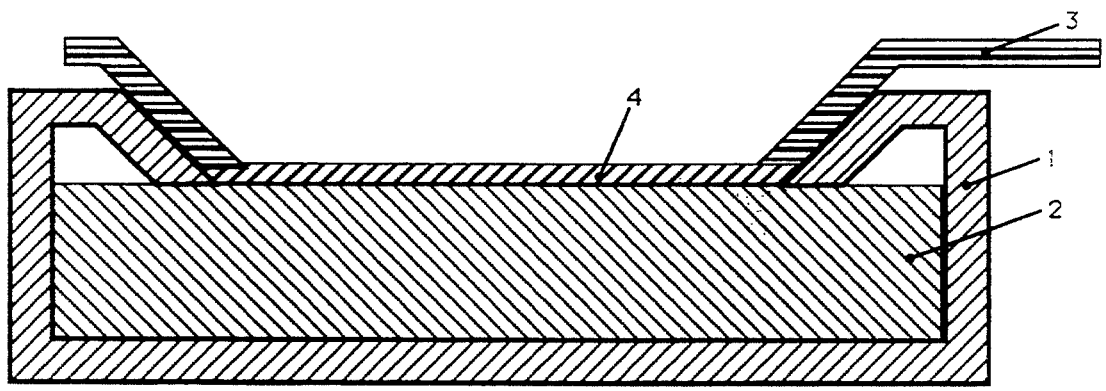
FIG. 1 is a cross-sectional view of a solid phase diagnostic device for use in the present invention.

The present invention is directed to a new assay procedure and also to new solid phase assay devices for use with a so-called physical developer.

In accordance with one aspect of the invention there is provided a new assay procedure for detecting the presence of an analyte in a fluid sample using a tracer having a metal label which signal is enhanced by applying a physical developer.

The assay is performed with a device having a support for a test area and having attached thereto a binder specific for the analyte to be detected. The assay comprises the steps of directing the fluid sample and the tracer through a porous medium into contact with the test area at a controlled flow rate to allow binding of the analyte with the binder and binding the tracer to the analyte, directing a physical developer through said porous medium to amplify the signal generated by the tracer, and separating the device to allow the test area to be read.

Ideally the fluid sample and tracer are caused to flow to the binder in a manner such that the sample contacts the binder, prior to substantial contact of the tracer with either the sample or binder. The addition of tracer may be followed immediately, or after a brief incubation to increase sensitivity by permitting greater binding of binder and tracer, by a washing step to remove unbound tracer. In the instant device the pores in the porous medium are of sufficiently large size to allow passage of said fluid sample, tracer and physical developer, but small enough to prevent passage of interfering substances present in the fluid sample and the physical developer. In physical contact and fluid communication with the support may also be an absorptive layer which acts to draw sample, tracer and physical developer through the support thereby bringing the analyte and tracer in contact with the binder. The latter absorptive layer also receives liquids and any analyte not bound at the test area on the support.

In a first preferred embodiment of the invention the porous medium is a separate filter and the test area is located on that side of the support facing the filter. The absorptive layer is in contact with the support on the side opposite the side on which the test area is located. In order to detect the presence of tracer on the support, the filter is removed and visibility of tracer is determined as a measure of analyte at the test area on the support. The latter is in direct correlation with the presence of analyte in the liquid sample.

In a second preferred embodiment of the invention the porous medium is the support and the test area is located on that side of the support in contact with the absorptive layer. In order to detect the presence of tracer on the support, the support and absorptive layer should be separated and the visibility of tracer is determined as a measure of analyte at the test area of the support. The latter is in direct correlation with the presence of analyte in the liquid sample.

Preferably the porous medium has pore sizes smaller than 12 microns, preferably smaller than 6 microns. The pore sizes should however be sufficient to allow passage of the tracer, therefore the pore size should be larger than 0.2 microns, preferably larger than 0.4 microns. By carefully selecting the pore size and the thickness of the filter and/or support not only the background staining at the test area can significantly be decreased but also the rate of reagent flow can be controlled to achieve a desired sensitivity and convenient rapid assay processing.

Those skilled in the art appreciate that the binder needs to be attached securely enough to stay on the support under assay conditions. Preferably the binder is attached to the test area in a concentration of at least ten micrograms per square centimeter. The preferred support is a nitrocellulose membrane having a pore size between 0.2 microns and 12 microns. Most preferably the support is nitrocellulose having a pore size between 0.2 and 5 microns, in particularly about 0.45 microns.

In accordance with another aspect of the invention the present invention provides solid phase assay devices for use with the above procedures.

Figure 2:
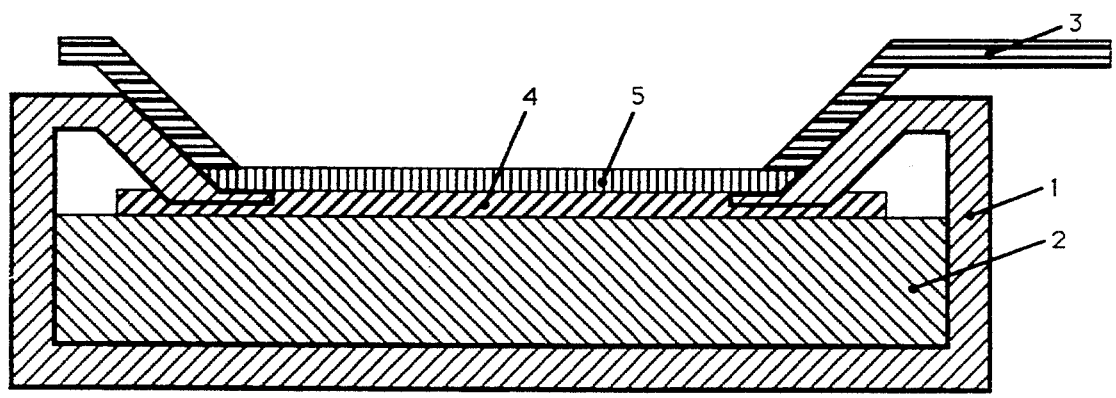
FIG. 2 is a cross-sectional view of an another solid phase diagnostic device for use in the present invention

The device for use in the first preferred embodiment, see for example FIG. 2, preferably has a support 4 having upper and lower surfaces and a test area on its upper surface. A removable filter 5 overlies the upper surface of said support. A binder is attached to the test area in a sufficient concentration to allow the tracer bound to the test area under assay conditions to become visible. Those skilled in the art appreciate that the binder needs to be attached securely enough to stay on the support under assay conditions. The preferred device further includes an absorptive layer 2 in fluid communication with the support 4 and the filter 5. The absorptive layer 2 receives liquids and any analyte and tracer not specifically bound at the test area. The absorptive layer 2 may also cooperate with the support and filter to control the flow of the reagents. In the instant device the filter 5 whereto the fluid sample, tracer and in particular the physical developer are applied has sufficiently small pore sizes to remove interfering substances which may be present in the fluid sample and the physical developer, and large enough pore sizes to allow passage of liquid and any analyte and tracer. It is clear that the support 4 ought to be sufficiently porous to allow passage of liquid and any analyte and tracer not specifically bound to the test area.

The device for use in the second preferred embodiment, see for example FIG. 1, preferably has a support 4 having upper and lower surfaces and a test area on its lower surface. A binder is attached to the test area in a sufficient concentration to allow the tracer bound to the test area under assay conditions to become visible. The preferred device further includes an absorptive 2 layer in fluid communication with the support. The absorptive layer 2 receives liquids and any analyte and tracer not specifically bound at the test area. The absorptive layer 2 may also cooperate with the support 4 to control the flow of the reagents. In the instant device the support 4 whereto the fluid sample, tracer and physical developer are applied should have sufficiently small pore sizes to remove interfering substances present in the fluid sample and in particular in the physical developer, and large enough pore sizes to allow passage of liquid and any an analyte and tracer not specifically bound to the test area. The device for use in the second preferred embodiment should be constructed in such a manner that the support 4 and the absorptive layer 2 can be detached from each other to enable detection of the bound tracer at the test area at the lower surface of the support 4. Ideally the above devices should be part of an appropriate holder 1. Such holders may take a variety of shapes but should preferably include a means 3 of separating the layers to enable reading of the assay. Such means preferably takes the form of a press fitted carder comprising either the filter, as in FIG. 2, or the support, as in FIG. 1, having the test area on its lower surface.

Surprisingly, when the construction of the devices is controlled as described above, the amplification of the signal of the tracer bound to the test area with a physical developer results in distinct coloured signal with a neglectable background staining at and around the test area. Control of the pore sizes and surface areas as described above even allow to achieve a visible readout of difficult to detect analytes at the test area after physical development. The test devices and procedures of the present invention are acceptable for use in virtually any specific binding assay format and protocol. The devices and procedures are suitable for use in qualitative and quantitative procedures.

The porous medium, in particularly the filter layer of the first preferred embodiment and the support of the second preferred embodiment, may include any porous material which is able to entrap and/or capture from the reagents those substances, other than tracer, on which metal ions may be deposited during the physical development. Such substances include in particular metal nuclei and insoluble metal salts which are present in the developer or other fluid reagent. In an known devices these substances frequently give rise to an unacceptable background noise at the test area of the support.

The pore size and thickness of the porous medium is preferably controlled. in a manner such that the flow of liquids through the test area provides the requisite sensitivity as well as a rapid and accurate assay. The pore size and the corresponding rate of flow selected for the filter and/or support are dependent upon the expected range of analyte concentration and the analytes binding affinity with binder and/or tracer. As the expected range of analyte concentration increases, the pore size and flow rate may increase.

The porous medium is preferably dimensioned in size and a manner such that the flow rate of the physical developer through the test area is at least 0.01 ml/min, and generally no more than 60 ml/min. A particularly preferred flow rate is between 0.5 ml/min and 20 ml/min.

The choice of material of the filter layer is not critical provided that it has pores of sufficient size to allow constituents in the fluids applied to the assay, including tracer and analyte to pass through the layer to the test area. The filter may conveniently be made from a non-woven web having randomly oriented fibers such as nitrocellulose non woven webs or rayon non-woven webs.

The support for use in the present invention may be any one of those well know to persons skilled in the art provided that it is porous enough to allow fluids applied to the device to pass through the porous support to the absorptive layer. Additionally, the support needs to be constructed of a material that does not non-specifically bind constituents and chemicals in the sample and reagents.

Included within the support is the test area where the binder is securely attached. The test area may comprise the entire surface of the support or it may comprise only a portion of the support. Preferably, the test area comprises only a portion of the support and is surrounded by a background area which is free of binder. Those skilled in the art appreciate however that the test area should be large enough to support binder in a concentration whereby tracer specifically bound to the the test area under assay conditions becomes visible. The support and test area may be made of the same material or of different materials. The visual effect of a positive reaction at the test area may can also be enhanced by utilizing a readily distinguishable pattern. Preferably, the support is a nitrocellulose membrane and the test area is a portion of that membrane. The term "nitrocellulose" refers to nitric acid esters of cellulose, which may be nitrocellulose alone or a mixed ester of nitric acid and other acid being preferred. The supports which are formed from cellulose esterified with nitric acid alone, or a mixture of nitric acid in another acid such as acetic acid, are often referred to as nitrocellulose paper. The support has a mean pore size which is greater then the size of the particulate label employed in the tracer so that the tracer, which does not become bound under assay conditions, flows through the support to the absorptive layer and is not trapped or non-specifically bound in the test area. In general, the mean pore size should be at least 0.2 microns and preferably at least 0.4 microns. In general, the pore size does not exceed 12 microns. Other types of supports include Whatman 31 ET Chromatography Paper, nylon 66 such as Biodyne TM and PVDF (polyvinylidine fluoride) such as Immobilon TM. In regardwith the selection of the porous materials further reference is made to Electrophoresis (1986), 7, 1–18 and Journal of Immunological Methods (1984), 72, 313–340.

The material used as a binder on the test area is selected for the particular assay chemistry involved. Preferably, the binder is a specific binding species comprising one member of a specific binding pair, e.g., an antigen or antibody. Selection of a suitable binder is within the scope of those skilled in the art. Similarly, the methods for securely attaching a binder to a solid support are well known to those skilled in the art. Thus, the binder may be attached to the test area through covalent or non covalent bonding, directly or indirectly. Preferably, the binder is adsorbed to the test area.

In accordance with a preferred embodiment, the binder is an antibody securely attached to the test area by adsorption in a concentration of at least 1 microgram per square centimeter. The binder can be adsorbed in a concentration of at least 10 micrograms per square centimeter and preferably, at least 40 micrograms per square centimeter. In some cases, a polyhydroxy compound (e.g. glycerol, erythritol, or sorbitol) or a sugar (e.g. glucose or sucrose) may be included in a binder coating solution to prevent non specific binding during the assay. Similarly, the residual binding capacity of the test area and support may be blocked by treatment of the test area and support with one or more types of proteins which do not specifically bind the materials to the employed in the assay, e.g. bovine serum albumin. Wetting agents can also be used to ensure proper flow of assay reagents through the test area. Suitable wetting agents include sucrose and commonly available surfactants, e.g., non-ionic Tween 20 (Sigma chemicals).

The absorptive layer of the device can be made from any absorbing material. The absorptive layer needs to have absorbency capacity sufficient to absorb liquids applied to the test device during the assay. The absorbing material also should provide a driving force which causes reagents applied to the test area to flow into the absorptive layer. Suitable absorbing materials include cellulose absorbent pads having a capacity to absorb three to five milliliters of fluids per gram of pad.

Suitable absorbent material would include any of the so-called super absorbents such as those used in the diaper products, cellulose, cellulose acetate, rayon/cotton, polypropylene microporous plastic and any combination of cotton linter fibres such as Grade 470, GB003, GB004, or S300 from Schleicher and Schuell, the latter being most preferred.

In order to obtain a reasonable enhancement of the tracer bound at the test area the assay should be constructed in such a manner that the physical developer is in contact with the bound tracer for at least 1 sec, under normal assay conditions the contact will last longer than 5 sec, preferably more than 10 sec. The upper limit is less critical using the device of the present invention since the non-tracer induced reduction, the so-called "self-nucleation" at the test area becomes only apparent after a long development time. For example, in case an art-known physical developer is used with the device of the present invention no apparent background was noticed after 10 minutes of development. Therefore development time can easily be increased up to 30 minutes. In most instances a sufficient sensitivity can be obtained after on 1 min of development. Under preferred assay conditions the optimal sensitivity is obtained after 10 to 30 sec of physical development.

The physical developer is a solution containing a soluble metal salt and a reducing agent capable of improving the signal generated by the tracer. Suitable physical developers have been described in for example, the European Patent Publication No. 158,746 which corresponds to U.S. Pat. No. 4,775,636 incorporated herein by reference.

The reducing agents for use in said physical developer are meant to include any agent which reduces metal ions, preferably silver, gold, platinum, palladium or thallium ions, from a physical developer in proximity of an active site. Preferably said reducing agents form stable solutions with one or more constituents of the physical developer. As reducing agent there may particularly be mentioned, 1,2-dihydroxy-benzene, 1,4-dihydroxybenzene (Hydroquinone), 4-methylaminophenolsulfate (Metol TM), 4-aminophenol, 1,4-diaminobenzene, 1,2-diaminobenzene, N-(4-hydroxyphenyl)glycine, 2,4-diaminophenol, 1-phenyl-3-hydroxypyrazole (Phenidone TM) or mixtures thereof. As other constituents (adjuvants) of the physical developer there may be mentioned, buffers, preservatives, e.g., anti-oxidants or organic stabilizers, speed regulators, bactericides and the like, such as, for example, sodium sulfite, sodium bisulfite, sodium citrate and the like.

The tracer is a ligand labeled with a metal particle, preferably a colloidal gold label, with the ligand of the tracer capable of being bound directly or indirectly to the analyte which is bound to the supported binder. Preferably the ligand is a member of a specific binding pair, e.g., an antigen or antibody.

The metal label for use in the assay according to the invention is meant to include any particle which can catalyse the reduction of metal ions, resulting in a deposition of the corresponding metal particles at the site of the tracer. Often the thus disposed metal particles in turn catalyse the reduction, creating an autocatalytic process. The metal labels to be used comprise metals, metal compounds or polymers optionally coated or impregnated with metals or metal compounds which can catalyse directly or indirectly the reduction of metal ions on their surface. As examples of such metals there may be named gold, silver, thallium, platinum, palladium as well as copper, nickel and the like with gold being preferred. As examples of metal compounds there may be named their corresponding complexes and sulfides. Polymers coated or impregnated with metals or metal compounds have similar properties as the metal or metal compounds but size, density and metal content can be optimally combined. For use in the preferred assay the label should be selected so that specific ligand can be attached to the label without loosing its affinity for the analyte.

Particularly preferred label for use in the method according to the present invention are either (i) colloidal metal particles, optionally a sol, containing metals or metal sulfides; or (ii) metal chelates, especially those incorporating ethylenediaminotetraacetic acid (EDTA) or diethylenetriaminepentaacetic acid (DTPA) groups; or (iii) polymers optionally impregnated with metals or metal sulfides, e.g., polymerization products of benzidine derivatives such as, for example, diaminobenzidine polymers.

Experimentation has shown that a substantial range of colloidal gold may be utilized including from about 1 nm to about 55 nm with a preferred size range within the range of 2 to 20 nm and the most preferred size approximately in the neighbourhood of 4 to 10 nm.

The preparation of colloidal labels, in particular colloidal gold particles, their attachment to specific binding agents or any agents bindable thereby and the various methodologies of combining them, directly or indirectly, with the desired bindable substances are known. In this connection, reference may be made to U.S. Pat. No. 4,313,784; U.S. Ser. No. 660,832 which corresponds to the European Patent Publication No. 158,746; U.S. Ser. No. 744,091 which corresponds to the European Patent Publication No. 0,165,633; Immunohistochemistry, Cuello, A.C. (ed.), IBRO handbook series, Wiley, New York, 1983, pages 347 to 372 and Techniques in Immunocytochemistry Vol. 2, pages 217 to 284 (1983).

In general, the attachment is easily effected by contacting the particles with an aqueous medium of appropriate pH wherein the desired binding agents, e.g., antibodies, are dissolved. In order to protect the particles from non-selective interactions with nonspecific proteins of the test samples it may be appropriate to add to the aqueos medium quenching or stabilizing agents such as, for example, immunochemically inert polar macromolecules, e.g. bovine serum albumin (BSA), polyvinyl pyrrolidone (PVP) and polyethylene glycol (PEG). After a suitable period of time the unstabilized particles and free or loosely bound binding agents are removed by repeated centrifugation and washing. If desired, the particles can also be sized according to a procedure described in J. Cell Biol. 90, 533–536.

Alternatively, the proteins can also be covalently bound to the labels following the procedure described in U.S. Pat. No. 3,857,931 using a water soluble carbodiimide coupling agent.

The attachment of metal chelates to binding agents such as antibodies is easily carded out following methodologies described in for example, Analytical Biochemistry 142, 68–79 (1984) and in Cancer Research 45, 5694–5699 (1985). In general, reactions for coupling chelating agents such as diethylenetriaminepentaacetic acid (DTPA), ethylenediaminotetraacetic acid (EDTA) and the like to proteins include diazonium coupling and acylation with activated carboxyl groups. The thus obtained chelatorconjugated proteins retain their immunoreactivity and can easily be charged with the desired metallic element.

As polymers which could be used as label for use in the methods of the present invention there may be named the polymerization products of benzidine derivatives being optionally charged with metals or metal compounds. The use and preparation of diaminobenzidine polymers is described, for example in J. Histochem. Cytochem. 30, 183–184 (1982) and Neuroscience 13, 513–525 (1984).

The advantages of the above described new assays are clear since they offer all the advantages of the use of a physical developer, but without the disadvantages which result from the use of said developer in the art-known assays, including the characteristic criticality associated with washing, timing and ultra clean recipients.

Apart from eliminating the necessity of very clean contacting surfaces, e.g. vessels, analytical grade chemicals, ultra-pure water and multiple wash steps the present assays also enable a severalfold increase in the ratio between the tracer-specific signal and noise created by self-nucleation. As a result the sensitivity can be increased by keeping the tracer longer into contact with the physical developer, or the speed of the development can be increased. In some cases a combination of both increased overall speed and sensitivity can be implemented.

Because the filter, support and absorptive layer may be constrained to take virtually any shape an impressive variety of devices may be envisaged for a suitable presentation. The assays of the present invention can therefore easily be oriented towards use by experienced laboratory personnel as well as by non-technically trained people which may execute the assay carelessly.

Further understanding of the present invention can be derived from the following non limiting examples.

EXAMPLES

1.1. Preparation of Colloidal gold labelled anti-mouse immunoglobulin antibodies A colloidal gold sol with a mean diameter of 10 nm, Aurobeads G 10, was purchased from Janssen Biotech, B-2430 Olen Belgium. Affinity purified goat-anti-mouse Ig antibodies were dialyzed overnight at 4° C. against a 5 mM carbonate buffer of pH 9.2. The pH of the gold sol was brought to 9.0 with potassium hydroxide. 100 ml of this gold sol was stirred in a beaker at room temperature. 1 mg of the dialyzed antibodies was added. Two minutes later, 1 g bovine serum albumin (BSA) dissolved in 10 ml water and brought at pH 9.0. After 2 minutes, the gold conjugate was centrifuged at 4° C. for 1 hour at 15000x g. After removal of the supernatant, the pellet was resuspended in 100 ml 20 mM Tris-HCl at pH 8.2, containing 1% BSA and 150 mM NaCl. This suspension was centrifuged again, and the pellet was resuspended in the same buffer to a volume of which the optical density at 520 nm was about 5.0.

1.2. Preparation of a protected physical developer I

Two liquid components of this developer were prepared separately. Solution A was made by dissolving 12 g histidine, 0.4 g silver nitrate, 4 g sodium citrate and 4 g citric acid in 100 ml distilled water. Solution B consists of 3.34 g sodium citrate.2H$_2$O, 1.86 g tris(hydroxymethyl)aminomethan, 2 g sodium sulphite, 0.3 g p-methylaminophenol.hydrochloride, 0.4 g p-aminophenol.HCl in 100 ml distilled water.

1.3. Preparation of a protected physical developer II

Two liquid components of the developer were prepared separately. Solution A was made by dissolving 12 g histidine, 0.4 g silver nitrate, 4 g sodium citrate and. 4 g citric acid in 100 ml distilled water.

Solution B consists of 3.34 g sodium citrate.2H$_2$O, 1.86 g tris(hydroxymethyl)aminomethan, 2 g sodium sulphite, 2 g p-methylaminophenyl.hydrochloride in 100 ml distilled water.

1.4. Preparation of a protected physical developer II

Two liquid components of the developer were prepared separately. Solution A was made by dissolving 8 g imidazole, 0.18 g silver nitrate, 1.4 g sodium citrate(.H$_2$O) and 3.6 g citric acid (H$_2$O) in 100 ml distilled water. Solution B was made by dissolving 3.3 g sodium citrate (.H$_2$O), 1.0 g citric acid (H$_2$O), 0.5 g p-methylaminophenol.hydrochloride and 2.0 g sodium methasulphate in 100 ml distilled water.

1.5. Standard test procedure

A standard test procedure was executed in order to investigate some of the different parameters which influence the immunoassay procedure of the present invention. A nitrocellulose blotting membrane (2×2 cm) was spotted with mouse IgG as antigen. A concentration range of 250 microgram/ml to 1 microgram/ml was used. On the nitrocellulose sheet, spots of 1 microliter antigen were made. After drying the spots for 15 minutes the nitrocellulose was blocked during 60 minutes in a solution of dry milk (Carnation) or equivalent blocking products (Bovine serum Albumin) in a TRIS buffer 0.25 M Tris(hydroxymethyl)-aminomethan-0.001 g/l thimerosal-10 g/l dry milk. After the blocking step, the membranes were washed with distilled water and dried.

In order to evaluate the new approach, a simple flow-through device was assembled with absorbing tissue paper as moisture absorbing material. A small plastic test tube stop without bottom served as a sample application funnel. In the first series of experiments the spotted nitrocellulose membrane was put on top of the tissue with the antigen spot up. In the second series of experiments the nitrocellulose was put on the tissue paper with the antigen spot facing the tissue paper.

350 microliter Goat anti-Mouse IgG coupled to colloidal gold, prepared as described in 1.1., was added in the funnel. After the gold probe flowed through the filter, the filter was washed with 600 microliter distilled water. The gold signal was developed by mixing 300 microliter of solution A described in 1.4. with 300 microliter of solution B described in 1.4. When the liquid had passed the membrane, the membrane was washed by applying 600 microliter distilled on the filter.

1.6. Results

A black-brown signal was read on the membrane. For the first series it was read on top of the membrane (Table 2), for the new procedure it was read at the bottom of the membrane (Table 1 ). The obtained signal/noise ratio was much better for the new procedure. The results were quantified with a reflectometer (Barbieri Densi 301).

TABLE 1

| METHOD ACCORDING TO THE PRESENT INVENTION | | | | |
|---|---|---|---|---|
| conc. | spot | background | % noise/signal | % signal/noise |
| 500 | 0.57 | 0.07 | 12.3 | 8.1 |
| 250 | 0.62 | 0.09 | 14.5 | 6.9 |
| 125 | 0.60 | 0.15 | 25.0 | 4.0 |
| 62 | 0.51 | 0.10 | 19.6 | 5.1 |
| 31 | 0.45 | 0.13 | 28.9 | 3.5 |

TABLE 2

| | | PRIOR ART METHOD | | |
|---|---|---|---|---|
| conc. | spot | background | % noise/signal | % signal/noise |
| 500 | 0.68 | 0.21 | 30.9 | 3.2 |
| 250 | 0.67 | 0.16 | 23.9 | 4.2 |
| 125 | 0.62 | 0.26 | 41.9 | 2.4 |
| 62 | 0.62 | 0.16 | 25.8 | 3.9 |
| 31 | 0.4 | 0.19 | 47.5 | 2.1 |

As the silver enhancement proceeds, the gold particles are enhanced. After a certain reaction time silver particles are formed, which precipitate on the silver membrane, and give the filter a grey colour.

In the new approach the dissolved silver ions pass through the filter and enhance the gold particles; the bigger silver particles, which appear after a certain reaction time, cannot penetrate the membrane and stay on top of it. Evaluating the results we can observe that in the classical approach the non-specific silver precipitates disturb the visibility of the signal. In the new approach the specific signal can be judged without problems, because of the complete white background of the membrane. The nitrocellulose served in this experiment as a solid phase and as a filter to get rid of the undesired silver particles.

1.7. Modifications on the standard test method

In order to demonstrate the filtering effect of the solid phase the following experiment was performed: in one experiment we used a piece of nitrocellulose with the antigen spot upwards, in the other experiment we put a second nitrocellulose membrane on top of the solid phase membrane (also with antigen spot facing up). The standard test procedure as described in 1.5. was executed. In this experiment the second membrane served as a filter. The experiment proved that a similar improved signal/noise ratio can be obtained as in experiment 1.5, resulting in a higher sensitivity.

Another modification of the standard test procedure consists in omitting the washing step between the addition of the gold conjugate and the silver enhancement reagents. This approach further simplifies the method. Within this modification there was no background staining observed in the new proposed method. In the classical approach the membrane stained grey-black.

1.8. Influence of the Composition of the silver enhancement reagents

The influence of the composition of the protected physical developer was investigated.

The standard test method (1.5.) was executed using the solutions described in 1.2., 1.3. and 1.4. The results were not influenced by the composition of the protected physical developer. In all experiments the method of the present invention resulted in a much better background and signal-to-noise ratio which improved the sensitivity of the method.

We claim:

1. A method of detecting the presence of analyte in a fluid sample using a tracer having a colloidal metal label and in which the signal of the tracer is enhanced by applying a physical developer comprising:
    a) directing the fluid sample and the tracer through a porous medium into contact with a test area containing a binder specific for the analyte to be detected, at a controlled flow rate to allow reaction of the analyte with the binder and the tracer to the analyte;
    b) directing a physical developer through said porous medium and through said test area to amplify the signal generated by the tracer;
    c) washing the porous medium; and
    d) observing the signal generated by the tracer in the test area.

2. A method according to claim 1 wherein the pores in the porous medium are of sufficiently large size to allow passage of said fluid sample, tracer and physical developer, but small enough to prevent passage of interfering substances present in the fluid sample and the physical developer.

3. A method according to claim 1 comprising the additional step of absorbing liquids and unbound analyte after passage through the test area.

4. A method according to claim 1 or 3 wherein the pores in the porous medium are between 0.2 and 12 microns.

5. A method according to claim 1 or 3 wherein the test area comprises nitrocellulose having a pore size between 0.2 and 5 microns.

6. A method according to claim 1 or 3 wherein the metal label is a colloidal gold label having a particle size between 2 and 20 mm.

7. A method according to claim 1 or 3 wherein the physical developer comprises a soluble silver salt and a reducing agent.

* * * * *